United States Patent
Guarino

(10) Patent No.: US 11,229,779 B1
(45) Date of Patent: Jan. 25, 2022

(54) METHOD FOR SKIN LIGAMENT INJECTION TO OBTAIN A LIFTING EFFECT

(71) Applicant: Enrico Guarino, Miami, FL (US)

(72) Inventor: Enrico Guarino, Miami, FL (US)

(*) Notice: Subject to any disclaimer, the term of this patent is extended or adjusted under 35 U.S.C. 154(b) by 0 days.

(21) Appl. No.: 16/991,634

(22) Filed: Aug. 12, 2020

(51) Int. Cl.
*A61M 37/00* (2006.01)
*A61M 1/00* (2006.01)

(52) U.S. Cl.
CPC ........... *A61M 37/00* (2013.01); *A61M 1/0062* (2013.01); *A61M 1/84* (2021.05); *A61M 2037/0023* (2013.01); *A61M 2202/08* (2013.01); *A61M 2210/0606* (2013.01)

(58) Field of Classification Search
CPC .... A61M 37/00; A61M 1/0062; A61M 1/008; A61M 2037/0023; A61M 2202/08; A61M 2210/0606; A61M 1/84
See application file for complete search history.

(56) References Cited

U.S. PATENT DOCUMENTS

| | | | | |
|---|---|---|---|---|
| 9,931,445 | B2* | 4/2018 | Pustilnik | B01L 3/50825 |
| 10,363,080 | B2 | 7/2019 | Elkins | |
| 10,850,137 | B2* | 12/2020 | McGovern | A61Q 19/08 |
| 2009/0069739 | A1* | 3/2009 | Mohamed | A61B 18/14 |
| | | | | 604/20 |
| 2010/0104542 | A1* | 4/2010 | Austen, Jr. | A61K 35/35 |
| | | | | 424/93.7 |
| 2011/0213336 | A1* | 9/2011 | Cucin | A61B 10/02 |
| | | | | 604/522 |
| 2012/0189585 | A1* | 7/2012 | Giampapa | A61K 38/1825 |
| | | | | 424/93.7 |
| 2012/0277698 | A1* | 11/2012 | Andrew | A61M 1/0058 |
| | | | | 604/319 |
| 2013/0087643 | A1* | 4/2013 | Tremolada | C12M 45/02 |
| | | | | 241/24.1 |
| 2013/0150825 | A1* | 6/2013 | Rimsa | A61M 5/1452 |
| | | | | 604/506 |
| 2013/0317484 | A1* | 11/2013 | Chau | A61M 1/008 |
| | | | | 604/542 |
| 2015/0218506 | A1* | 8/2015 | Nash | C12M 47/02 |
| | | | | 435/379 |
| 2017/0035678 | A1* | 2/2017 | Otto | A61K 8/85 |

(Continued)

OTHER PUBLICATIONS

Peter Huang, "The True Lift Technique: facial ligament retightening, an anatomical approach", Jun./Jul. 2018, The PMFA Journal, vol. 5 No. 5.*

*Primary Examiner* — Theodore J Stigell
(74) *Attorney, Agent, or Firm* — Sanchelima & Associates, P.A.; Christian Sanchelima; Jesus Sanchelima

(57) ABSTRACT

A method for skin ligament injection incorporates the benefits of regenerative medicine to provide more natural and longer lasting results in the revitalization of a patient's face. The method includes a first phase in which through the use of aspiration tubes with reduced diameter, small aspiration holes and controlled aspiration pressure with aspiration in a superficial plane of the skin, a user collects tissue rich in stein cells with waste of fibrotic tissue. A second phase includes the sterile manipulation and washing of fat to collect only the tissue containing the stein cells arranged around vascular structures and growth factors collected inside organelles called exosomes. Lastly, a third and final phase includes injecting the obtained product into the skin of a patient.

7 Claims, 1 Drawing Sheet

(56) References Cited

U.S. PATENT DOCUMENTS

| | | | |
|---|---|---|---|
| 2018/0221550 A1* | 8/2018 | Pustilnik | A61L 27/3604 |
| 2018/0264043 A1* | 9/2018 | Pettine | A61K 9/0021 |
| 2019/0255229 A1* | 8/2019 | Hogue | G01N 15/0272 |
| 2020/0061258 A1* | 2/2020 | Khalaj | C12M 45/02 |

* cited by examiner

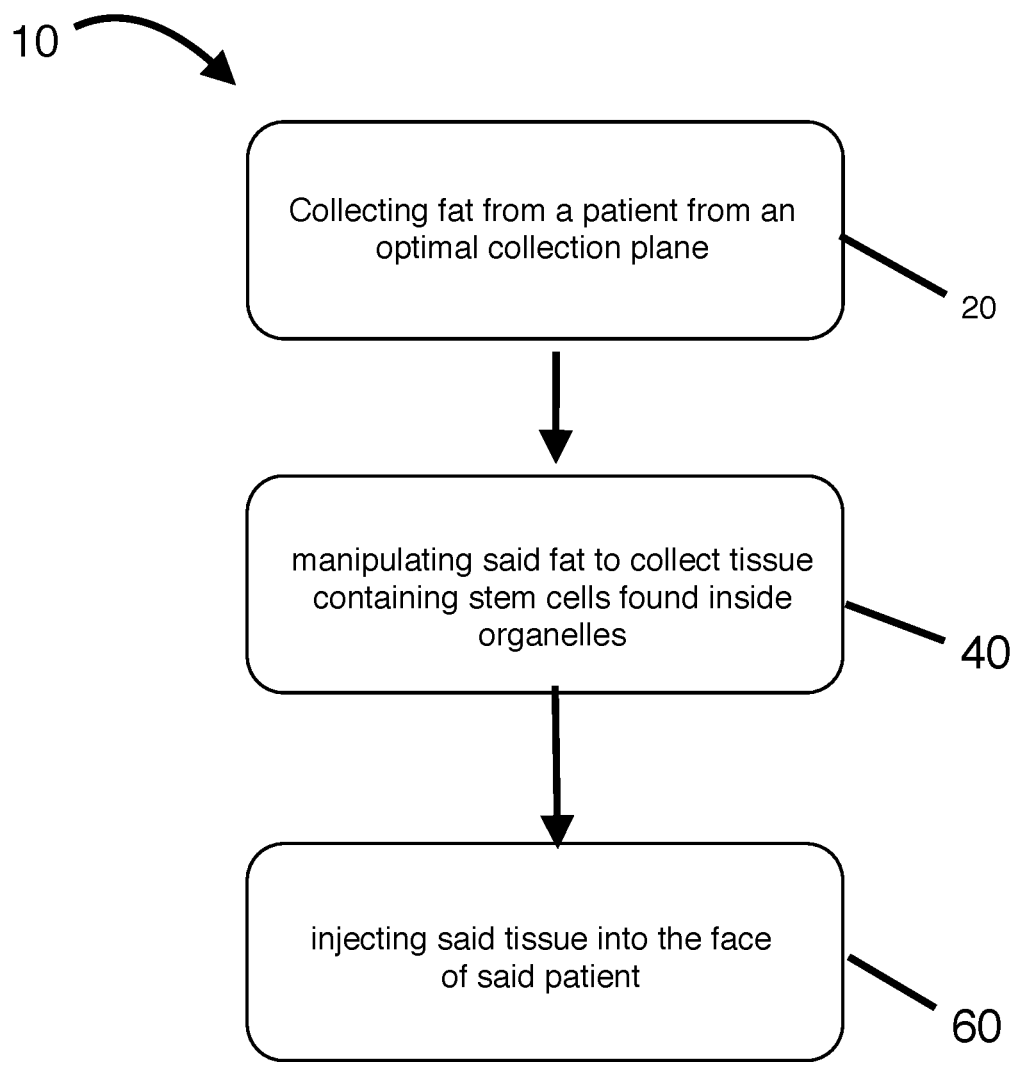

METHOD FOR SKIN LIGAMENT INJECTION TO OBTAIN A LIFTING EFFECT

BACKGROUND OF THE INVENTION

1. Field of the Invention

The present invention relates to a method for skin ligament injection and, more particularly, to a method for skin ligament injection to obtain a lifting effect that uses fat to induce a localized volume effect and a regeneration effect.

2. Description of the Related Art

Several designs for a method for skin ligament injection have been designed in the past. None of them, however, include a method for skin ligament injection that incorporates the benefits of regenerative medicine to provide more natural and longer lasting results in the revitalization of a patient's face. The method includes a first phase in which through the use of aspiration tubes with reduced diameter, small aspiration holes and controlled aspiration pressure with aspiration in a superficial plane of the skin, a user collects tissue rich in stein cells with waste of fibrotic tissue. A second phase includes the sterile manipulation and washing of fat to collect only the tissue containing the stein cells arranged around vascular structures and growth factors collected inside organelles called exosomes. Lastly, a third and final phase includes injecting the obtained product into the skin of a patient. It is known that one of the most popular aesthetic trends is a non-invasive procedure known as facial contouring where the face is re-structured, and sags are lifted through the use of gel filler injections to lift the skin. The procedure further reduces folds and wrinkles to create a brighter and younger looking face. However, there is an increased demand for treatments that give more natural and longer lasting results that are not achieved through facial contouring. Therefore, there is a need for a method for skin ligament injection that incorporates the benefits of regenerative medicine to obtain a more natural and longer lasting aesthetic results.

Applicant believes that a related reference corresponds to U.S. Pat. No. 10,363,080 issued for devices, systems, and methods to treat cosmetic defects, and often apply cooling with at least one tissue-penetrating probe inserted through the skin of a patient. The cooling may remodel one or more target tissue so as to effect a desired change in a composition of the target tissue and/or a change in its behavior. However, the cited reference differs from the present invention because it fails to teach of fat skin ligament injection method which includes extracting tissue from a patient rich in stein cells. The extracted tissue is then washed and manipulated to collect only the tissue containing the stein cells. Lastly the isolated tissue is injected into a patient to provide a longer lasting and natural revitalized effect.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a skin ligament injection method which provides a more natural and longer lasting facial aesthetic procedure over the facial contouring procedure.

It is another object of this invention to provide a skin ligament injection method which combines a localized volume effect and the regeneration effect of stein cell regenerative medicine.

It is still another object of the present invention to provide a skin ligament injection method which utilizes the regenerative effect of the stein cells in the ligament due to adult mesenchymal cells that can be transformed in connective tissue that produces new collagen and elastin fiber.

It is yet another object of this invention to provide such a method that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a flow chart for a method 10 containing first step 20, second step 40, and third step 60 in accordance to an embodiment of the present invention.

DETAILED DESCRIPTION OF THE EMBODIMENTS OF THE INVENTION

Referring now to the drawings, where the present invention is generally referred to with numeral 10, it can be observed a skin ligament injection method 10 which basically includes a first step 20, a second step 40, and a third step 60.

Regenerative medicine encompasses innovative therapies that allow the body to repair or regenerate aging cells, tissues and organs. The skin is a particularly attractive organ for the application of novel regenerative therapies due to its easy accessibility. Among these therapies, stein cells and platelet-rich plasma (PRP) have garnered interest based on their therapeutic potential in scar reduction, antiaging effects, and treatment of alopecia.

Stem cells possess the cardinal features of self-renewal and plasticity. In the present embodiment, self-renewal refers to symmetric cell division generating daughter cells identical to the parent cell. Furthermore, plasticity is the ability to generate cell types other than the germline or tissue lineage from which stem cells derive. Stem cells can be categorized according to their differentiation potential. Totipotent stem cells may develop into any primary germ cell layer such as ectoderm, mesoderm, endoderm of the embryo, as well as extraembryonic tissue such as the trophoblast which gives rise to the placenta. Plutipotent stem cells such as embryonic stem cells have the capacity to differentiate into any derivative of the three germ cells layers but have lost their ability to differentiate into the trophoblast.

Adults lack totipotent or pluripotent cells, they have multipotent or unipotent cells. Multipotent stem cells are able to differentiate into multiple cell types from similar lineages. Mesenchymal stem cells (MSCs), for example, can differentiate into adipogenic, osteogenic, chondrogenic, and myogenic cells. Unipotent stem cells have the lowest differentiation potential and can only self-regenerate. Adult stem cells are self-originating (defined as being taken from the patient himself/herself) and can be multiplied in an appropriate medium in which to grow. Once the stem cells are put in contact with the right stimulating factors, they will differentiate in the cell line required.

One of the tissues of the human body richest in these cells is represented by the fat that contains up to 500 MSCs for each square centimeter present throughout the patient's life (i.e. normal fat tissue). Therefore, for the purposes of this specification, an optimal collection plane of the human body will be defined as any area of fat that contains up to 500 MSCs for each square centimeter. The presence of these cells throughout a patient's lifetime allows the fat to be utilized in order to collect powerful stein cells for patients of all ages. The number of and quality of this fat tissue tends to decrease with the passage of time and therefore greater attention must be paid to the collection and processing the further a patient continues to age. Over the past few years in the field, numerous devices and methods have been developed for the collection and processing of fat with the aim of having the purest fat material.

First step 20 includes the collecting of tissue rich in stein cells with waste of fibrotic tissue destined for death after being injected into the recipient tissue. In one embodiment, this tissue is collected through the use of aspiration tubes with reduced diameter, with small aspiration holes, and controlled aspiration pressure in a superficial plane of the skin for the collection of the tissue. In one implementation, a 2 mm cannula connected to guide is used to suction the fat in an optimal collection plane of the patient. The optimal placement of the cannula is provided as two centimeters from the skin to obtain the best quality of fat while maintaining safe suction such that the guide does not allow to change the plane of the tube downwards or upwards. Additionally, the tube has holes which may implement a diameter of 1.2×2 mm with a blunt surface to avoid trauma and bleeding under the skin. This measurement allows for the optimal size for the collection of the purest fat possible with little waste tissue.

Second step 40 is represented by the sterile manipulation and washing of fat to collect only the tissue containing the stein cells. The stein cells in the tissue are arranged around vascular structures and growth factors collected inside organelles called exosomes. There are several FDA approved devices currently on the market which are capable of performing this procedure. In one embodiment, the MiniTC kit from jointechlabs is used for manipulating the fat. The device allows for the processing of lipoaspirate to obtain the desired tissue for method 10. This process allows for the obtaining of fat that includes an engraftment and survival percentage greater than 95%.

Third step 60 is represented by an injection phase in which the obtained product is injected into a patient. There are different options and injection techniques that can be utilized depending on the desired result. The present invention features a new injection technique called lypo-gold injection in which well-defined quantities of nano fat are injected into routine areas such as skin ligaments of the face. The well-defined quantities of nano fat are tissue that is derived from 800-micron mesh filtration. The objective of lypo-gold injection is to create a lifting effect in the injection area of the ligament to the skin and therefore to re-position the tissue naturally and without excessive volume. Additionally, the use of the tissue rich in mesenchymal cells after some time produces both fibroblasts as well as connective tissue cells capable of restoring tone and ligament support. Fibroblasts are skin cells responsible for the production of collagen, hyaluronic acid and elastin which are the main extra cellular components that determine skin elasticity and texture. Once the injection of the ligament fat is complete, a superficial injection of a product is performed with micro-injections with the aim of regenerating the skin with restoration of the elasticity of tone and color.

The described method, if properly performed allows one to obtain results that are evident starting from the second or third month and that can be maintained for over two years. Furthermore, the newly injected cells may be nourished periodically to maintain optimal results with an additional retouch provided after the first 9-12 months. The present invention can additionally be combined with other techniques already known to practicing plastic surgeons.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for skin ligament injection to obtain a lifting effect, comprising:
   a. collecting fat from a patient from a collection plane;
   b. manipulating said fat to collect tissue containing stem cells found inside organelles; and
   c. injecting said tissue into skin ligaments of the face of said patient.

2. The method for skin ligament injection to obtain a lifting effect of claim 1 wherein said collection plane is an area of fat that contains up to 500 mesenchymal stem cells for each square centimeter.

3. The method for skin ligament injection to obtain a lifting effect of claim 1 further including a superficial injection of a product performed with micro-injections into the face.

4. The method for skin ligament injection to obtain a lifting effect of claim 1 further including placing a cannular at least two centimeters from said patient's skin to collect said fat.

5. The method for skin ligament injection to obtain a lifting effect of claim 1 wherein said tissue obtained by manipulating said fat includes an engraftment and survival percentage greater than 95%.

6. The method for skin ligament injection to obtain a lifting effect of claim 1 wherein said tissue that was injected is retouched after 9-12 months.

7. A method for skin ligament injection to obtain a lifting effect, consisting of:
   a) collecting fat from a patient from a collection plane by placing a cannular at least two centimeters from said patient's skin to collect said fat, wherein said collection plane is an area of fat that contains up to 500 mesenchymal stem cells for each square centimeter;
   b) manipulating said fat to collect tissue containing stem cells found inside organelles, wherein tissue obtained by manipulating said fat includes an engraftment and survival percentage greater than 95%; and
   c) injecting said tissue into skin ligaments of the face of said patient, wherein a superficial injection of a product is additionally performed with micro-injections into of the face.

* * * * *